US00PP14538P29

(12) United States Plant Patent
Khanuja et al.

(10) Patent No.: US PP14,538 P2
(45) Date of Patent: Feb. 17, 2004

(54) MINT PLANT NAMED 'SAMBHAV'

(50) Latin Name: *Mentha arvensis*
Varietal Denomination: Sambhav

(75) Inventors: Suman Preet Singh Khanuja, Lucknow (IN); Ajit Kumar Shasany, Lucknow (IN); Sunita Dhawan, Lucknow (IN); Mahendra Pandurang Darokar, Lucknow (IN); Sarita Satapathy, Lucknow (IN); Tiruppadiripuliyur Ranganathan Santha Kumar, Lucknow (IN); Dharmendra Saikia, Lucknow (IN); Nirmal Kumar Patra, Lucknow (IN); Janak Raj Bahl, Lucknow (IN); Arun Kumar Tripathy, Lucknow (IN); Sushil Kumar, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/482,645

(22) Filed: Jan. 18, 2000

(51) Int. Cl.[7] ..... A01H 5/00
(52) U.S. Cl. ..... Plt./259

(58) Field of Search ..... Plt./259

(56) References Cited

U.S. PATENT DOCUMENTS

PP10,935 P * 6/1999 Kumar et al. ..... Plt./259
PP12,030 P2 * 8/2001 Kumar et al. ..... Plt./259

OTHER PUBLICATIONS

S.P.S. Khanuja, et al., *A Rapid procedure for isolating somaclones of altered genotypes in Mentha arvensis.,* J. Med. Aroma. Plant Sci. 20 (1998) 359–361.
A.K. Shansany, et al. *High regenrative nature of Mentha arvensis internodes.,* Journal of Biosciences 23 (1998) 641–646.

* cited by examiner

*Primary Examiner*—Bruce R. Campell
*Assistant Examiner*—W C Haas
(74) *Attorney, Agent, or Firm*—Ladas & Parry

(57) ABSTRACT

The present invention relates to a novel, insect tolerant, high yielding essential oil and menthol yielding mint plant named 'Sambhav', which is a cultivar of *Mentha arvensis* L.. The mint plant of the present invention has been developed as a result of planned experiments which devised a procedure for early selection of somaclonal variants at the in vitro stage of the variety of *Mentha arvensis*.

3 Drawing Sheets

Botanical designation: *Mentha arvensis* L.

BACKGROUND OF THE INVENTION

1. Field of the Invention

The origin of the mint plant of the present application is a single somaclonal variant of cultivar 'Himalaya' (U.S. Plant Pat. No. 10,935). The present invention relates to a novel, insect tolerant, high yielding essential oil and menthol yielding mint plant named 'Sambhav', which is derived from *Mentha arvensis* L.. The mint plant of the present invention has been developed as a result of planned experiments for the development of an insect tolerant mint plant with high oil and menthol yield which devised a procedure for early selection of somaclonal variants at the in vitro stage variety of *Mentha arvensis*. The plant of the present invention can be propagated vegetatively by suckers and is genetically stable for commercial cultivation. The plant type of the present invention is unique because it has an extra wide canopy and height surpassing all existing varieties. This allows for better sunlight capture and foliage production which ultimately produce high oil and menthol yield.

2. Description of Related Art

*Mentha arvensis* L. var *piperescens* Holmes (menthol or Japanese mint) is an industrial crop that is widely cultivated for its essential oil from which menthol is purified by crystallization through freezing. Menthol and other terpenoids present in the dementholated oil of *Mentha arvensis* are used in the food, perfumery and pharmaceutical industries. In the varietal improvement programme, the genetic alternations leading to the enhancement in the tolerance against pest and disease and improvement of other characteristics which improve the yield and quality of essential oil is most desirable. Insect tolerance is desired particularly against *Spilarctia obliqua* in *Mentha arvensis* L., one of the most damaging pests of mints in India. Since the mint plant is of considerable interest to the industrial world, programs for the isolation of desirable clones with improved terpene accumulation and suitable agronomic traits are being pursued in several laboratories. However, due to the inherent problem of seed setting in mints, conventional breeding programs are severely hampered. In vitro high efficiency procedures for cell and callus cultures and shoot regeneration from axillary buds and leaf explants have been reported in some species of the genus Mentha, especially the commercially important species *M. piperata* and *M. spicata*. However, in *M. arvensis* proliferation from limited explants such as nodes, terminal and axillary buds and distal segments of leaf petiole have relatively low levels of efficiency. There have been attempts to develop new varieties or genotypes by alternative methods like clonal selection, mutation breeding and somaclonal variation in mint plants (S. P. S. Khanuja, A. K. Shasany, S. Dhawan, S. Kumar, Rapid procedure for isolating somaclones of altered genotypes in *Mentha arvensis*. J Med. Aroma. Plant Sci. 20 (1998) 359-361.). Applicants have reported high efficiency protocols for rapid detection and selection procedures for development of somaclonal variants through molecular approaches in *Mentha arvensis* (S. P. S. Khanuja, A. K. Shasany, S. Dhawan, S. Kumar, Rapid procedure for isolating somaclones of altered genotypes in *Mentha arvensis*. J Med. Aroma. Plant Sci. 20 (1998) 359-361). Applicants have also successfully defined the condition and media to restrict the emergence of somaclonal variation for stable micropropagation purposes (A. K. Shasany, S. P. S. Khanuja, S. Dhawan, U. Yadav, S. Sharma, S. Kumar, High regenerative nature of *Mentha arvensis* internodes. Journal of Biosciences 23 (1998) 641646.).

SUMMARY OF THE INVENTION

For the present invention, Applicants utilize the already reported protocol (S. P. S. Khanuja, A. K. Shasany, S. Dhawan, S. Kumar, Rapid procedure for isolating somaclones of altered genotypes in *Mentha arvensis*. J Med. Aroma. Plant Sci. 20 (1998) 359-361.) to generate capture the somaclonal variations in larger frequencies. Applicants then screen the somaclones for their tolerance to *Spilarctia obliqua* by using a novel method for rapid and dependable selection of tolerant clone(s) at the tissue culture stage. The somaclones that were determined to be insect tolerant were then subjected to screening using instar larvae of lepidopteran insect pest *Spilarctia obliqua*.

The selected tolerant pants are then tested for their stability, essential oil content, menthol content and biomass yield. Consequently, the plant 'Sambhav' was selected for unmatchable vigor of shoots, higher menthol production and increased insect tolerance through field evaluation.

Accordingly, the invention provides a novel mint plant of *Mentha arvensis* named 'Sambhav', which is developed employing tissue culture techniques, said plant of the present invention possessing the following combination of characteristics:

a. the plant is highly tolerant to foliage feeding insect pests, especially *Spilarctia obliqua;* b. the plant possesses vigorous and rapid vegetative growth with high regenerability covering at least a 85 cm canopy area and a height of at least 73.5 cm attained in a maximum of 100 days;

c. the plant has a distinct molecular profile by random amplified polymorphic DNA (RAPD) using 20 OPJ primers and 20 MAP primers which distinguishes the plant from the other existing varieties, d. the plant shows tolerance to leaf spots, rust and powdery mildew as in the parent variety 'Himalaya', e. the plant has the follows characteristics: light greenish leaves, whitish flowers with a distinct morphology of a single main stem with branches coming out of the lower nodes imparting a shape of up-side down open filled umbrella to the canopy allowing equal distribution of sunlight, thus prevents yellowing and fall of lower leaves;

f. the plant is able to produce the highest herbage when compare to the other control plants, and g. the plant yields oil containing 75 to 80% menthol;

The plant of the present invention is developed through an unique, rapid in vitro screening method. This method is not limited to *Mentha arvensis*.

BOTANICAL DESCRIPTION OF THE PLANT 'SAMBHAV'

Figure 1:
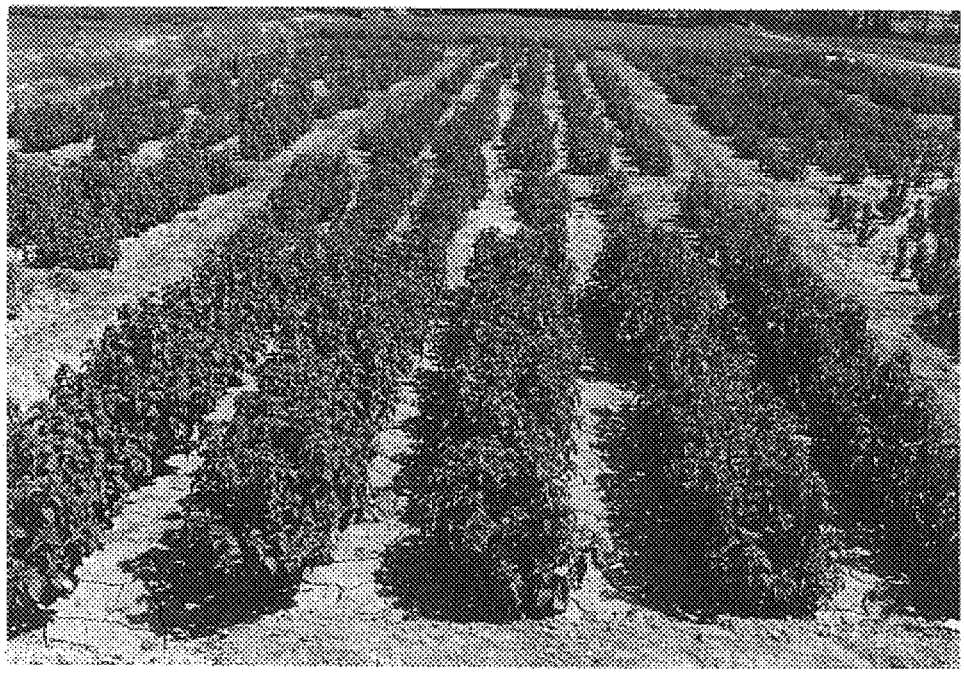
FIG. 1 shows field views of the morphological features of the 'Sambhav' plants at 70 days.
Figure 2:
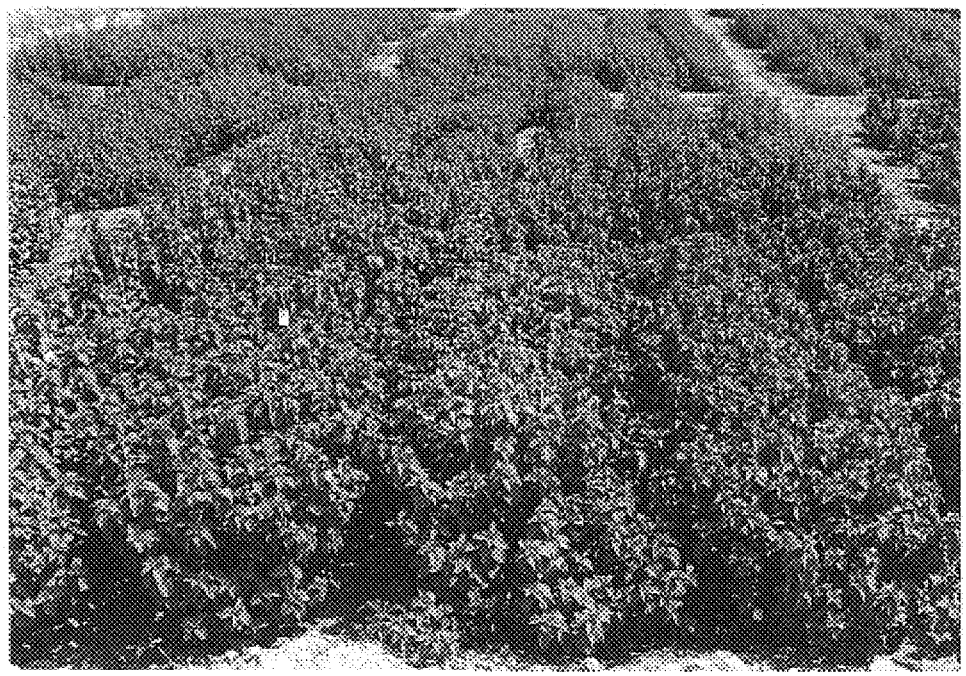
FIG. 2 shows field views of the morphological features of the 'Sambhav' plants at 100 days.
Figure 3:
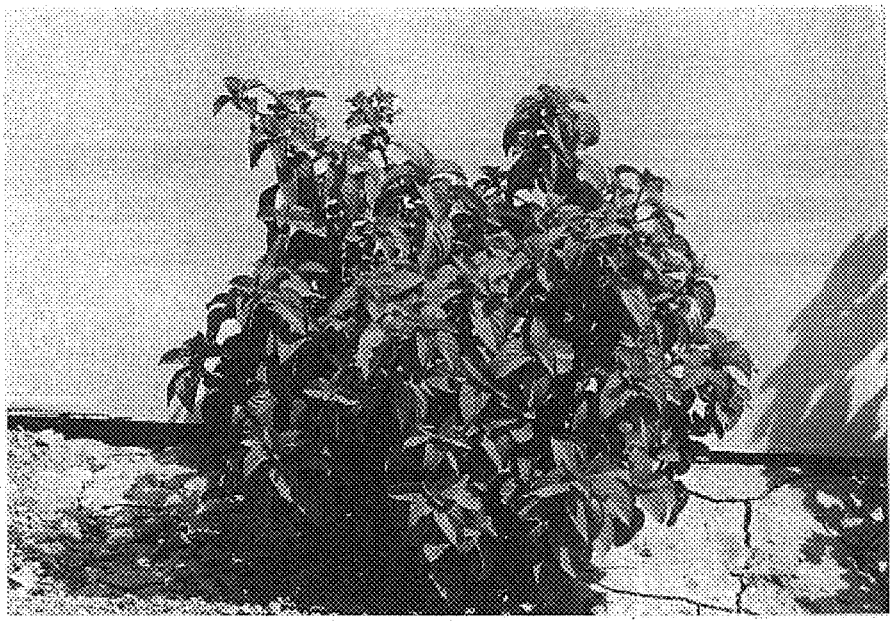
FIG. 3 shows the rapid growth of the 'Sambhav' plant and its canopy at 70 days.
Figure 4:
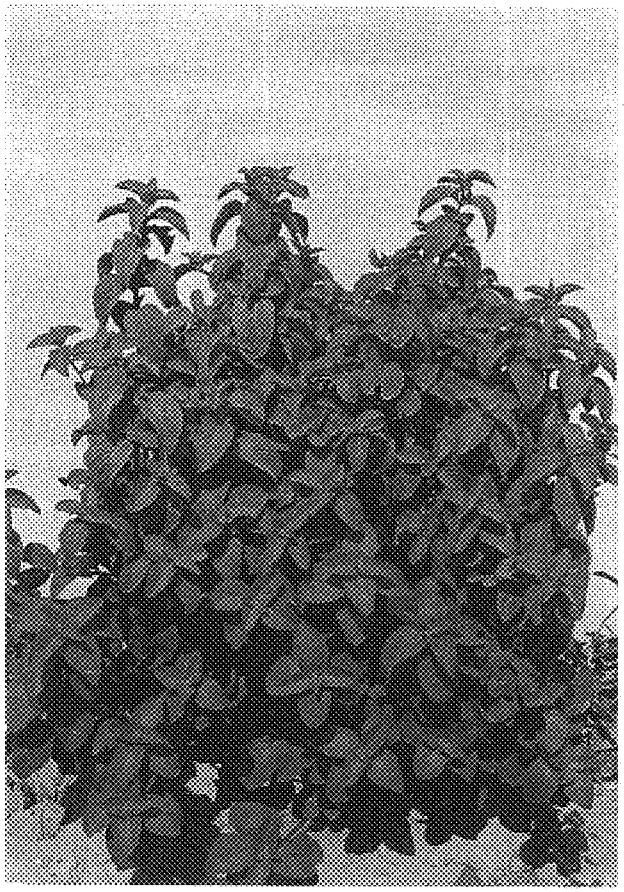
FIG. 4 shows the rapid growth of the 'Sambhav' plant and its canopy at 100 days.

1. Genus: Mentha.
2. Species: *arvensis* L.
3. Family: Lamiaceae.
4. Common name: Japanese mint/corn mint/menthol mint.
5. Plant height: 73.5±3.27 cm.
6. Plant canopy: 85–90 cm.

A. Stem:

*1. Shape.*—Round to quadrangular, hard, woody.
*2. Unit of branches (main, upper, middle, lower) Number of Fingers.*—Right hand: 5. Left hand: 5.
*2. Number of branches.*—7 to 24.
*3. Main branch.*—18 to 37.
*4. Upper branch (30th node).*—3 to 6.
*5. Middle branch (20th node).*—3 to 8.
*6. Lower branch (10th node).*—4 to 10.
*7. Main branch (From lower to upper nodes in cm).*—1.0 to 6.0.

B. Leaf:

*Apex shape acute.*—Base shape Attenuate.
*Shape.*—Lacerate.
*Surface.*—Hairy and rough.
*Texture.*—Moderately thick and rigid.
*Margin.*—Moderately deep serration (14 to 50 numbers).
*Size.*—Moderately broad.
*Area.*—16.1 $cm^2$ (the average leaf lamina area of 41 leaves of a single branch).
*Length.*—8.56±0.56 cm.
*Width.*—5.51±0.34 cm.
*Petiole length.*—1.7±0.17 cm.
*Fragrance.*—Methanol smell.
*Vein.*—Colour green (144A).
*Colour of surface.*—Light green (137B) for upper surface, Yellow green (139C) or lower surface.
*Number of trichomes per leaf.*—1280.
*Trichome ratio (lower leaf/upper leaf).*—3.10.

C. Time of flowering: April–May (60 to 70 days after planting first flowering detected).

D. Lasting of blooms: Continue till harvesting (110 days after planting).

E. Flowers: Arranged in whorls surrounding the stem at the base of lateral leaves.

*1. Size.*—4.65 mm long.
*2. Flower shape.*—Tubular.
*3. Inflorescence size.*—Continues to grow as indefinite racemose.
*4. Pedicel length.*—1.1 to 2.5 mm.
*5. Pedicel colour.*—Yellow green (145C).
*6. Calyx diameter.*—1 mm, four fused.
*7. Calyx colour.*—Yellow green group (145B).

8. *Corolla.*—Purplish white, four, fused to a bell shaped corolla tube (76C–D), 3 to 4 mm long.
9. *Anthers.*—Four, ocidimetary, come out of the corolla tube.
10. *Stigma.*—Bifid, Purple (76A).
11. *Colour of ovaries.*—Yellow green group (151A).
12. *Oil content in the fresh herb* (%).—0.77 to 0.8.
13. *Oil quality.*—Menthol content (%): 75 to 80%. Congealing point: 2 to 21° C.

*Herbage* (*Shoot biomass* (*Q/100 m*$^2$).—2.10

Bihar hairy caterpillar (*Spilarctia obliqua*) is a pest of a polyphagus nature which infects mint crops frequently in Terai and in the northern Indian plains. The infestation is sometimes so heavy and unmanageable that it may lead to more than 80% complete loss of foliage and consequently the oil yield proportionately. Therefore, it is desirable to explore the possibility of developing insect tolerant high yielding clones of mint plants. The popular menthol producing mint plant variety 'Himalaya' developed in 1996 by Central Institute of Medicine and Aromatic Plants (hereinafter referred to as CIMAP) (U.S. Plant Pat. No. (10,935). This was the beginning of specific improvements in insect tolerance through generation of somaclonal variation while simultaneously looking for improved plant type with higher essential oil and menthol yields.

Encouraged by Applicants' own initial leads in the laboratory for rapid detection and isolation of somaclonal variants by using the protocol (S. P. S. Khanuja, A. K. Shasany, S. Dhawan, S. Kumar, Rapid procedure for isolating somaclones of altered genotypes in *Mentha arvensis*. J Med. Aroma. Plant Sci. 20 (1998) 359-361), Applicants generated 3000 independent somaclones. These clones were subjected to detection of molecular variation at the tissue culture stage through RAPD profiling. The DNA was isolated from 40 mg of leaf tissue and Polymerase chain reactions (PCRs) were carried out in 25 $\mu$l volume in a reaction tube containing 25 ng of DNA, 0.2 unit of Taq DNA polymerase, 100 pl each of dNTPs, 1.5 mM $MgC_{12}$ and 5 p mol of decanucleotide primers. The amplifications were carried out using a thermal cycler (MJ Research, USA). The amplified products were loaded in 1.2% agarose gel containing 0.5 $\mu$g ml$^{-1}$ of ethidium bromide and photographed by Polaroid system. Twelve decamer primers having the Sequence ID NOs 1–12 AAATCGGAGC (SEQ ID NO:1), GTCCTACTCG (SEQ ID NO: 2), GTCCTTAGCG (SEQ ID NO:3), TGCGCGATCG (SEQ ID NO:4), AACGTACGCG (SEQ ID NO:5), GCACGCCGGA (SEQ ID NO:6), CACCCTGCGC (SEQ ID NO:7), CTATCGCCGC (SEQ ID NO:8), CGGGATCCGC (SEQ ID NO:9), GCGAATTCCG (SEQ ID NO: 10), CCCTGCAGGC (SEQ ID NO: 11), CCAAGCTTGC (SEQ ID NO:12) were used to analyze all the in vitro regenerated clones. Out of 3000 regenerated clones, 245 showed variations at the DNA level in the RAPD profiles compared to the control plant "Himalaya".

The individual molecular variants selected through the RAPD analysis of somaclones were then subjected to screening against the larvae of lepidopteran insect pest *Spilarctia obliqua*.

Figure 5:
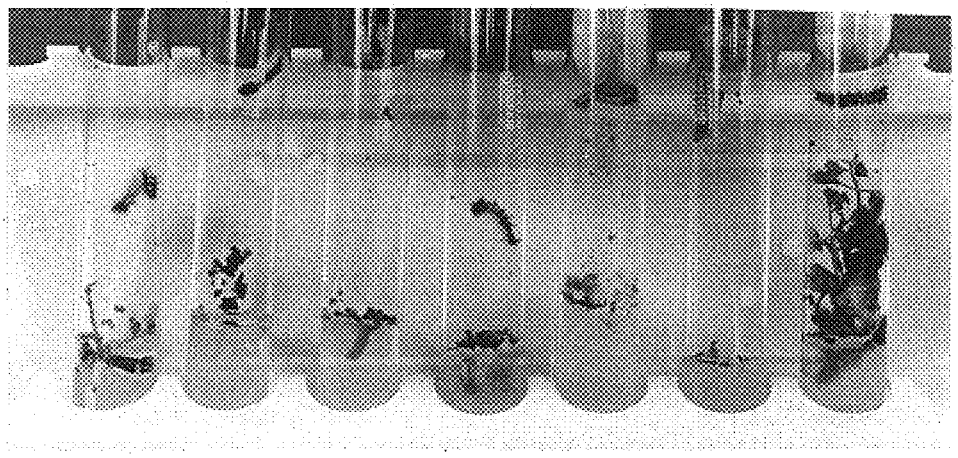
FIG. 5 shows instar larvae infected individual clones of other plants in comparison with clone of 'Sambhav'. Instar larvae is larvae that attacks mint plants.
Figure 6:
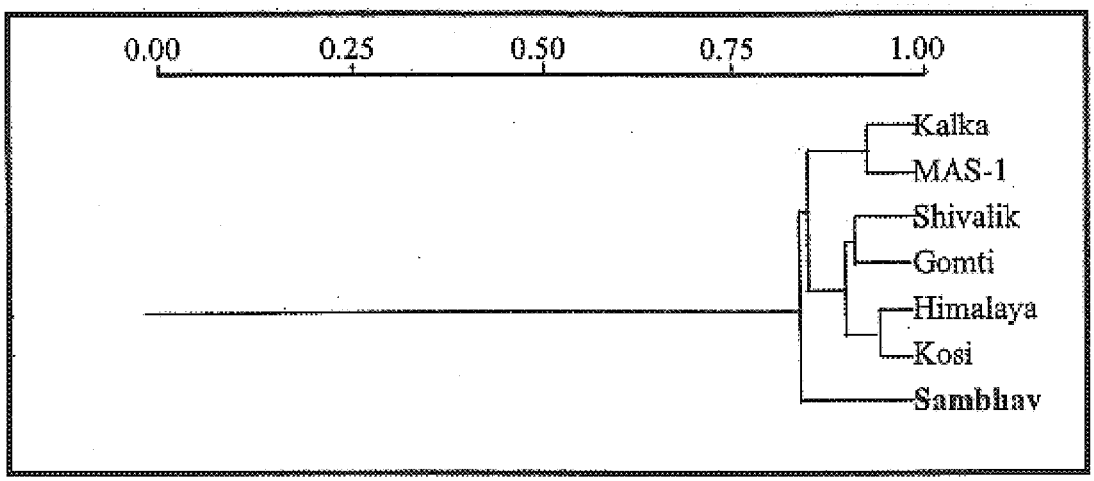
FIG. 6 shows the Genetic similarity of the new clone 'Sambhav' with other varieties of *Mentha arvensis*.

For this purpose, a new strategy was devised by subjecting the in vitro growing clones to attack by actively feeding 3$^{rd}$ instar larvae. The larvae were released right in the culture tubes containing individual clones on the rooting medium (FIG. 5). Most of the shoots of the clones were eaten away by these larvae within 2–3 days. However, three clones showed the least feeding by the larvae. In these tubes, only initial bites could be observed and nonfeeding was also conspicuous by typical symptoms of stalled growth in the starved larvae. These larvae were then transferred to other clone tubes, where they resumed feeding. This led Applicants to believe that the three clones must have some characteristics not liked by the feeding larvae. So Applicants again confirmed this by releasing another set of actively feeding 4$^{th}$ instar larvae into the tubes containing these three identified clones. This process was repeated three times and each time, the larvae showed non-preference to the clones and stopped feeding.

Applicants then hardened these three "insect-non-preferred" clones namely, CIMAP/GRB 1-06, 'Sambhav' and CIMAP/GRB 5-15 and transferred them to the glass-house in pots. Among these three clones, 'Sambhav' showed growth characteristics that were much higher in height and shoot proliferation. 'Sambhav' (This GRB) was multiplied in vitro from interodal explants through stable micropropagation protocol developed in the laboratory (A. K. Shasany, S. P. S. Khanuja, S. Dhawan, U. Yadav, S. Sharma, S. Kumar, High regenerative nature of *Mentha arvensis* internodes. Journal of Biosciences. 23 (1998) 641-646.) for genetic uniformity into about 1000 plantlets. Randomly 100 regenerated shoots from the clone were tested for variation in their profiles using the above described 12 random primers. Complete uniformity was observed among these clones without any variation from the control mother plant 'Sambhav' but the profiles were clearly distinct from other mint varieties including 'Himalaya'.

Breeding History

The plant 'Sambhav' can be propagated vegetatively through suckers for cultivation. The plant was developed by performing the RAPD analysis, selecting different somaclones followed by force feeding by insect to screen for insect tolerance character. The selected plant was grown in the glass house and the suckers obtained were field planted for multiplication. The suckers from the multiplication plots were taken for planting in the main field for field trials. Replicated field trials were conducted following normal agromonic practices by planting multiplied suckers in January 1998 and January 1999 in RBD fashion. Different growth and yield characteristics were recorded. For field trials, 10 m×10 m plots were prepared by adding only FYM 1.5 ton per ha. The field experiments were carried out in the farm field of CIMAP.

The seeds and fruits were not checked as the plant is propagated vegetatively through suckers.

The plants of the present invention was described after 100 days of planting during the month of May when the maximum temperature remained between 32 to 42° C. and the minimum temperature remained between 25 and 32° C.

The overall objective of the present invention was not only to develop insect tolerant genotypes but to simultaneously also have a better plant type with high menthol content and herbage yield for better productivity. So, the plant of present invention was tested in the field for oil yield, menthol content and herbage production against the checks. Replicated field trials were conducted following normal agronomic practices by planting multiplied suckers in January, 1998 and January, 1999 for 2 consecutive years in RBD fashion and diffent growth and yield characteristics were recorded (Table. 1). For field trials, 10 m×10 m plots were prepared by adding only FYM 1.5 ton per ha. Astonishingly, the 'Sambhav' was able to out-compete all existing varieties in its rate of growth. It was so rapidly growing that it could cover the inter-row spacing of 80 cm completely within a period of 90–100 days, which was not the case for the other control varieties taken (FIG. # 2). The plant canopy covered a space of 85 to 90 cm in 110 days in comparison to Himalaya(62–70 cm), Shivalik (50–56 cm) (unpatented), Gomti (70–75) (unpatented); Kosi (65–72) U.S. Plant Pat. No. 12,426, Kalka (40–60 cm) (unpatented) MAS-1(40–50 cm) (unpatented). This was the most desirable advantage to the plant because it produced the highest amount of oil and menthol.

Natural infestation of *Spilarctia obliqua* in the field absent insecticidal spray was noted in both the 1998 and 1999 crop stands. The clone 'Sambhav' had less than 10% leaf damage compared to 86% in the case of Gomti, 58% in Himalaya, 50% in Kosi in 1998. A similar trend was also recorded in 1999 when leaf damage was 70%, 50% and 46% for Gomti, Himalaya and Kosi respectively, compared to 6% in case of GRB 'Sambhav'. The plant of the present invention also produced the highest amount of essential oil per unit area in comparison to the other control plants in both successive yield trials. The total menthol yield consequently, was the highest due to more oil and herbage yield (Table 1). The plant was named 'Sambhav' (means "Possible") because the expression of its genotype made this a rare but most desirable combination of traits.

Thus, the plant of the present invention 'Sambhav' has a very high tolerance to *Spilarctia obliqua* attack, high growth rate and regenerability and produces the highest total herbage, oil and menthol yield per unit area in comparison to the other control plants and thereby being a unique and novel genotype which can be exploited for commercial cultivation superior to other available mint varieties for menthol production.

TABLE 1

Comparative growth and yield characteristics of plant of invention "Sambhav" (GRB 2-18) in relation to the existing Japanese mint varieties

| Property | Himalaya | Shivalik | MAS-1 | Kalka |
|---|---|---|---|---|
| Plant height (cm) | 60.9 + 6.2 | 68.25 + 3.4 | 43.2 + 1.1 | 51.6 + 2.7 |
| Canopy (cm) | 62–70 | 50–56 | 40–50 | 40–60 |
| Leaf number | 40.2 + 4.2 | 49.6 + 4.8 | 40.0 + 1.4 | 38 + 2.0 |
| Branch length | 40.4 + 6.8 | 44.2 + 8.7 | 36.6 + 9.0 | 45 + 9.7 |
| Branch number | 29.2 + 4.0 | 22.4 + 1.7 | 13.6 + 1.7 | 27.2 + 1.1 |
| Leaf length | 7.1 + 0.5 | 7.3 + 0.3 | 7.5 + 1.0 | 7.4 + 0.8 |
| Leaf breadth | 4.5 + 0.2 | 5.0 + 0.2 | 3.8 + 0.5 | 4.0 + 0.3 |
| Petiole length | 1.75 + 0.3 | 1.40 + 0.1 | 1.6 + 0.5 | 1.5 + 0.5 |
| Oil % | 0.7 | 0.5 | 0.5 | 0.8 |
| Menthol % | 80 | 77 | 88 | 82 |
| Herbage yield (Q per 100 $m^2$) | 1.25 | 0.75 | 0.50 | 0.80 |
| Oil yield (Kg per 100 $m^2$) | 0.85 | 0.35 | 0.27 | 0.64 |

| Property | Gomti | Kosi | Sambhav |
|---|---|---|---|
| Plant height (cm) | 74.2 + 7.3 | 66.2 + 3.1 | 73.5 + 3.3 |
| Canopy (cm) | 70–75 | 65–72 | 85–90 |
| Leaf number | 46.0 + 2.8 | 50.4 + 3.8 | 44.2 + 2.2 |
| Branch length | 58.4 + 14.6 | 52.0 + 5.7 | 50.1 + 8.8 |
| Branch number | 28.4 + 2.9 | 30.4 + 1.7 | 35.1 + 2.8 |
| Leaf length | 7.7 + 0.6 | 7.40 + 0.7 | 8.6 + 0.6 |
| Leaf breadth | 4.7 + 0.2 | 4.60 + 0.5 | 5.50 + 0.3 |
| Petiole length | 1.4 + 0.1 | 1.4 + 0.3 | 1.70 + 0.2 |
| Oil % | 0.5 | 0.8 | 0.8 |
| Menthol % | 73 | 76 | 77 |

TABLE 1-continued

Comparative growth and yield characteristics of plant of invention "Sambhav" (GRB 2-18) in relation to the existing Japanese mint varieties

| | | | |
|---|---|---|---|
| Herbage yield (Q per 100 $m^2$) | 1.60 | 1.70 | 2.10 |
| Oil yield (Kg per 100 $m^2$) | 0.83 | 1.42 | 1.61 |

TABLE 2

Comparison of "Sambhav" with other existing varieties of the same botanical and market class of *Mentha arvensis*

| Character | cv.MAS-1 | cv.Kalka | cv.Shivalik |
|---|---|---|---|
| 1. Leaf:stem ratio | 1.2 | 1.0 | 0.8 |
| 2. Stem | | | |
| colour | Upper green (141C), lower pigmented red purple (71B) | GREEN (141C), lower pigmented red purple (71B) | Green (141B) lower pigmented red purple (71B) |
| Stiffness | Hard | Hard | Woody |
| Thickness at 5th internode (mm) | 6.8 | 3.6 | 10.0 |
| 3. Leaf | | | |
| Colour | Green (139C) | Green (139C) | Green (138A) |
| Length (cm) | 6.46 | 6.7 | 5.2 |
| Width (cm) | 2.3 | 2.4 | 2.8 |
| Area ($cm^2$) | 8.2 | 8.7 | 10.1 |
| 4. Petiole length (cm) | 1.1 | 1.2 | 0.6 |
| 5. Flower colour | Whitish | Whitish | Whitish |
| 6. Flower length (mm) | 3.72 | 3.48 | 4.66 |
| 7. Calyx colour | Green (143B) with red purple streaks (71B) | Green (143B) with red purple streaks (71B) | Green (141B) |
| 8. Stigma colour | White | White | Purplish (71C) |
| 9. Disease incidence to | | | |
| Rust | Tolerant | Resistant | Susceptible |
| Alternaria leaf blight | — | Resistant | Susceptible |
| Corynespora leaf spot | Susceptible | Tolerant | Susceptible |
| Powdery mildew | Susceptible | Susceptible | Tolerant |
| 10. Pest infestation | | | |
| *Spilarctia obliqua* | Susceptible | Susceptible | Susceptible |

| Character | cv.Gomti | cv.Himalaya | cv.Sambhav |
|---|---|---|---|
| 1. Leaf:stem ratio | 1.0 | 1.5 | 1.7 |
| 2. Stem | | | |
| colour | Green (143B) lower pigmented purple (77A) | Green (143C) lower purplish (70A) | Green (144A) lower purplish (59B) |
| Stiffness | Woody | Hard | Woody |
| Thickness at 5th internode (mm) | 7.9 | 8.0 | 10.0 |
| 3. Leaf | | | |
| Colour | Green (138A) | Green (138B) | Green (137B) |
| Length (cm) | 6.4 | 6.2 | 8.6 |
| Width (cm) | 3.1 | 3.6 | 5.1 |
| Area ($cm^2$) | 13.3 | 15.4 | 16.1 |
| 4. Petiole length (cm) | 0.7 | 1.5 | 1.7 |
| 5. Flower colour | Whitish | Pinkish white | Purplish white (76C) |
| 6. Flower length (mm) | 4.74 | 3.72 | 4.65 |
| 7. Calyx colour | Green (141B) | Green (143C) | Green (145B) |
| 8. Stigma colour | Purplish (71C) | White | Purple (76A) |
| 9. Disease incidence to | | | |
| Rust | Susceptible | Resistant | Resistant |

TABLE 2-continued

| Comparison of "Sambhav" with other existing varieties of the same botanical and market class of *Mentha arvensis* | | | |
|---|---|---|---|
| Alternaria leaf blight | Susceptible | Resistant | Resistant |
| Corynespora leaf spot | Susceptible | Tolerant | Tolerant |
| Powdery mildew | Tolerant | Tolerant | Tolerant |
| 10. Pest infestation | | | |
| *Spilarctia obliqua* | Highly Susceptible | Susceptible | Tolerant |

The plant genotype 'Sambhav' of the present invention is a herbaceous perennial with a single tall upright stem possessing several lateral branches coming out from the lower nodes laterally rising in a fashion to give a shape of an open filled umbrella turned upside down. This special arrangement of branches facilitates the distribution of the captured sunlight equally to all the leaves and hence avoids shading, reducing lower leaf fall, which prevents economic loss to the plant. The chromosome number of the plant is 2n=96. The colour codes are in accordance with the "R.H.S. colour chart" published by The Royal Horticultural Society, 80 Vincent Square, London SW1P 2PE, 1995.

Evidence of uniformity and stability

No variants of any kind (morphological or molecular) has been observed since 1997 indicating the stability and uniformity of the genotype. Further, the comparative herbage and oil yields of 'Sambhav' were significantly higher in comparison to other varieties/genotypes in different years and seasons. Due to vigorous vegetative growth this genotype can be harvested earlier without reducing the yield of herbage, oil or menthol. The traits of insect tolerance against *S. obliqua* is unprecedented and stable.

Statement of distinction

The genotype 'Sambhav' possesses a very high level of insect tolerance against leaf damage by *S. obliqua* larvae, which is unique and unprecedented by any known variety. Additionally, it has a distinct canopy of one straight main stem with many lower branches arranged like an open filled umbrella turned upside down which is characteristic to this genotype only. The genotype of the present invention has the highest biomass and highest oil yield unit area in comparison to others. The total menthol yield of the new genotype is higher per unit area in comparison to other genotypes. Its genetic make up is distinct in terms of the DNA profile.

Randomly Amplified Polymorphic DNA analysis

The RAPD profiles of the plant 'Sambhav' establish its distinct identity as completely different from the parent plant 'Himalaya' as well as the known released varieties. The plant of the present invention was developed by screening molecular variants among somaclones already differentiated as distinct, unique and novel at the DNA level. The plant of the present invention has desirable morphological and economical traits in a rare unmatchable combination and is available only by Applicants in CIMAP. No variation in the RAPD patterns was observed in the analysis of the micropropagated as well as field raised population in successive generations indicating the stability of the genotype. The 20 MAP primers (MAP 01 to MAP 20) with the Sequenc ID NOs 1–20 AAATCGGAGC (SEQ ID NO:1), GTCCTACTCG (SEQ ID NO:2), GTCCTTAGCG (SEQ ID NO:3), TGCGCGATCG (SEQ ID NO:4), AACGTACGCG (SEQ ID NO:5), GCACGCCGGA (SEQ ID NO:6), CACCCTGCGC (SEQ ID NO:7), CTATCGCCGC (SEQ ID NO:8), CGGGATCCGC (SEQ ID NO:9), GCGAATTCCG (SEQ ID NO:10), CCCTGCAGGC (SEQ ID NO:11), CCAAGCTTGC (SEQ ID NO:12), GTGCAATGAG (SEQ ID NO:13), AGGATACGTG (SEQ ID NO:14) AAGATAGCGG (SEQ ID NO:15), GGATCTGAAC (SEQ ID NO:16), TTGTCTCAGG (SEQ ID NO:17), CATCCCGAAC (SEQ ID NO:18), GGACTCCACG (SEQ ID NO:19), AGCCTGACGC (SEQ ID NO:20) and 20 OPJ primers (Operon Technologies Inc, USA) were used for the analysis and similarity indices were computed to generate a similarity matrix among existing varieties and the plant 'Sambhav' (Table 3) The OPJ primers (01 to 20) were obtained from Operon technologies, USA. The MAP primers were used to develop a unique and distinct RAPD profile of the Plant.

TABLE 3

Similarity indices of different control plants analyzed in comparison to 'Sambhav'

| Gomti | Himalaya | Kosi | MAS-1 | Kalka | Shivalik | Sambhav |
|---|---|---|---|---|---|---|
| 1.00 | | | | | | |
| 0.90 | 1.00 | | | | | |
| 0.89 | 0.94 | 1.00 | | | | |
| 0.91 | 0.92 | 0.92 | 1.00 | | | |
| 0.85 | 0.88 | 0.85 | 0.89 | 1.00 | | |
| 0.92 | 0.93 | 0.91 | 0.90 | 0.87 | 1.00 | |
| 0.87 | 0.73 | 0.78 | 0.82 | 0.83 | 0.84 | 1.00 |

TABLE 4

Genetic similarity of the new clone 'Sambhav' with other varieties of *Mentha arvensis*.

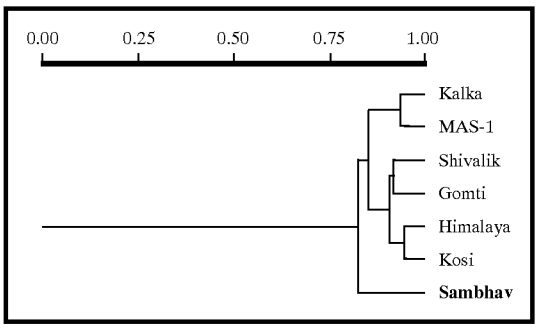

From RAPD analysis, the profiles were studied and similarity indices were calculated which were put into a matrix. This matrix was used to produce a graphic phenogram by means of UPGMA (unweighted pair group method with arithmetic average) cluster analysis (FIG. 1). As represented in the phenogram the clone of the invention is quite different from the other varieties. The diversity of the genotype of the plant of invention 'Sambhav' is 13%, 28%, 22%, 18%, 17% and 16% from the varieties Gomti, Himalaya, Kosi, MAS-1, Kalka and Shivalik. The highest difference in terms of polymorphic profiles was observed for the genotype of the invention with the parent plant 'Himalaya' from which it was developed as a somaclone. The plant genotype of the invention 'Sambhav' was most similar in terms of polymorphism with Gomti. In total the distinctiveness of the clone in RAPD profiles was established as total polymorphism detected.

Comparison of Sambhav with the check varieties

The new genotype 'Sambhav' was so rapidly growing that it could cover the inter-row spacing of 80 cm completely within a period of 90–100 days, which was not the case of other control varieties taken (FIG. # 2). The plant canopy covered a space of 85 to 90 cm in 110 days in comparison to Himalaya (62–70 cm), Shivalik (50–56 cm), Gomti (70–75), Kosi (65–72), Kalka (40–60 cm) and MAS-1__ (40–50 cm). The herbage yield of the plant 2.8 Q per 100 $m^2$ against 1.25, 0.75, 0.50, 0.80, 1.60, 1.70 for Himalaya, Shivalik, MAS-1, Kalka, Gomti and Kosi. Similarly the oil yield was highest (0.8%) in case of the genotype. The genotype though has less menthol percentage, when the total menthol yield per 100 $m^2$ is estimated by converting the total oil yield per 100 $m^2$ against the menthol percentage (77× 1.61/100) and it comes to 1.24 kg, which is much higher than other varieties. The menthol yield values for other varieties are 0.68, 0.27, 0.24, 0.52, 0.60,1.08 kg per 100 $m^2$ for Himalaya, Shivalik, MAS-1, Kalka, Gomti and Kosi respectively. This was the most desirable economical advantage to the plant with commercial value as it produced highest amount of herbage when compared to the other control plants and ultimately the oil and menthol per unit area in comparison to other genotypes while being the most tolerant to insect pest attack.

SEQUENCE LISTING

```
<160> NUMBER OF SEQ ID NOS: 20

<210> SEQ ID NO 1
<211> LENGTH: 10
<212> TYPE: DNA
<213> ORGANISM: Artificial Sequence
<220> FEATURE:
<223> OTHER INFORMATION: MAP Primer

<400> SEQUENCE: 1

aaatcggagc                                                          10


<210> SEQ ID NO 2
<211> LENGTH: 10
<212> TYPE: DNA
<213> ORGANISM: Artificial Sequence
<220> FEATURE:
<223> OTHER INFORMATION: MAP Primer

<400> SEQUENCE: 2

gtcctactcg                                                          10


<210> SEQ ID NO 3
<211> LENGTH: 10
<212> TYPE: DNA
<213> ORGANISM: Artificial Sequence
<220> FEATURE:
<223> OTHER INFORMATION: MAP Primer

<400> SEQUENCE: 3

gtccttagcg                                                          10


<210> SEQ ID NO 4
<211> LENGTH: 10
<212> TYPE: DNA
<213> ORGANISM: Artificial Sequence
<220> FEATURE:
<223> OTHER INFORMATION: MAP Primer

<400> SEQUENCE: 4

tgcgcgatcg                                                          10


<210> SEQ ID NO 5
<211> LENGTH: 10
<212> TYPE: DNA
<213> ORGANISM: Artificial Sequence
<220> FEATURE:
```

-continued

<223> OTHER INFORMATION: MAP Primer

<400> SEQUENCE: 5 aacgtacgcg 10

<210> SEQ ID NO 6
<211> LENGTH: 10
<212> TYPE: DNA
<213> ORGANISM: Artificial Sequence
<220> FEATURE:
<223> OTHER INFORMATION: MAP Primer

<400> SEQUENCE: 6 gcacgccgga 10

<210> SEQ ID NO 7
<211> LENGTH: 10
<212> TYPE: DNA
<213> ORGANISM: Artificial Sequence
<220> FEATURE:
<223> OTHER INFORMATION: MAP Primer

<400> SEQUENCE: 7 caccctgcgc 10

<210> SEQ ID NO 8
<211> LENGTH: 10
<212> TYPE: DNA
<213> ORGANISM: Artificial Sequence
<220> FEATURE:
<223> OTHER INFORMATION: MAP Primer

<400> SEQUENCE: 8 ctatcgccgc 10

<210> SEQ ID NO 9
<211> LENGTH: 10
<212> TYPE: DNA
<213> ORGANISM: Artificial Sequence
<220> FEATURE:
<223> OTHER INFORMATION: MAP Primer

<400> SEQUENCE: 9 cgggatccgc 10

<210> SEQ ID NO 10
<211> LENGTH: 10
<212> TYPE: DNA
<213> ORGANISM: Artificial Sequence
<220> FEATURE:
<223> OTHER INFORMATION: MAP Primer

<400> SEQUENCE: 10 gcgaattccg 10

<210> SEQ ID NO 11
<211> LENGTH: 10
<212> TYPE: DNA
<213> ORGANISM: Artificial Sequence
<220> FEATURE:
<223> OTHER INFORMATION: MAP Primer

<400> SEQUENCE: 11 ccctgcaggc 10

-continued

<210> SEQ ID NO 12
<211> LENGTH: 10
<212> TYPE: DNA
<213> ORGANISM: Artificial Sequence
<220> FEATURE:
<223> OTHER INFORMATION: MAP Primer

<400> SEQUENCE: 12 ccaagcttgc 10

<210> SEQ ID NO 13
<211> LENGTH: 10
<212> TYPE: DNA
<213> ORGANISM: Artificial Sequence
<220> FEATURE:
<223> OTHER INFORMATION: MAP Primer

<400> SEQUENCE: 13 gtgcaatgag 10

<210> SEQ ID NO 14
<211> LENGTH: 10
<212> TYPE: DNA
<213> ORGANISM: Artificial Sequence
<220> FEATURE:
<223> OTHER INFORMATION: MAP Primer

<400> SEQUENCE: 14 aggatacgtg 10

<210> SEQ ID NO 15
<211> LENGTH: 10
<212> TYPE: DNA
<213> ORGANISM: Artificial Sequence
<220> FEATURE:
<223> OTHER INFORMATION: MAP Primer

<400> SEQUENCE: 15 aagatagcgg 10

<210> SEQ ID NO 16
<211> LENGTH: 10
<212> TYPE: DNA
<213> ORGANISM: Artificial Sequence
<220> FEATURE:
<223> OTHER INFORMATION: MAP Primer

<400> SEQUENCE: 16 ggatctgaac 10

<210> SEQ ID NO 17
<211> LENGTH: 10
<212> TYPE: DNA
<213> ORGANISM: Artificial Sequence
<220> FEATURE:
<223> OTHER INFORMATION: MAP Primer

<400> SEQUENCE: 17 ttgtctcagg 10

<210> SEQ ID NO 18
<211> LENGTH: 10
<212> TYPE: DNA
<213> ORGANISM: Artificial Sequence
<220> FEATURE:

-continued

```
<223> OTHER INFORMATION: MAP Primer

<400> SEQUENCE: 18

catcccgaac                                                          10


<210> SEQ ID NO 19
<211> LENGTH: 10
<212> TYPE: DNA
<213> ORGANISM: Artificial Sequence
<220> FEATURE:
<223> OTHER INFORMATION: MAP Primer

<400> SEQUENCE: 19

ggactccacg                                                          10


<210> SEQ ID NO 20
<211> LENGTH: 10
<212> TYPE: DNA
<213> ORGANISM: Artificial Sequence
<220> FEATURE:
<223> OTHER INFORMATION: MAP Primer

<400> SEQUENCE: 20

agcctgacgc                                                          10
```

I claim:

1. A new and distinct variety of *Mentha arvensis* plant, as herein illustrated and described.

* * * * *